United States Patent
Hamrick

(10) Patent No.: US 9,499,839 B2
(45) Date of Patent: *Nov. 22, 2016

(54) METHODS FOR FERMENTING CARBOHYDRATE-RICH CROPS

(71) Applicant: Edward Brian Hamrick, Sunny Isles Beach, FL (US)

(72) Inventor: Edward Brian Hamrick, Sunny Isles Beach, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/966,650

(22) Filed: Dec. 11, 2015

(65) Prior Publication Data

US 2016/0097062 A1 Apr. 7, 2016

Related U.S. Application Data

(63) Continuation of application No. 14/940,390, filed on Nov. 13, 2015.

(60) Provisional application No. 62/139,881, filed on Mar. 30, 2015, provisional application No. 62/127,637, filed on Mar. 3, 2015.

(51) Int. Cl.
| | |
|---|---|
| *C12P 7/06* | (2006.01) |
| *C12P 7/14* | (2006.01) |
| *C08B 37/00* | (2006.01) |
| *C08B 30/04* | (2006.01) |

(52) U.S. Cl.
CPC ............... *C12P 7/06* (2013.01); *C08B 30/04* (2013.01); *C08B 37/0003* (2013.01); *C08B 37/0054* (2013.01); *C12P 7/14* (2013.01)

(58) Field of Classification Search
CPC ........................................................ C12P 7/06
See application file for complete search history.

(56) References Cited

U.S. PATENT DOCUMENTS

| | | | |
|---|---|---|---|
| 2,084,229 A | 6/1937 | Van Maanen | |
| 2,807,560 A | 9/1957 | Brownell et al. | |
| 4,328,043 A | 5/1982 | Freytag et al. | |
| 4,560,659 A * | 12/1985 | Asturias | C12P 7/06 435/161 |
| 6,656,287 B2 | 12/2003 | Sanders | |
| 8,318,453 B2 | 11/2012 | Medoff | |
| 8,669,064 B2 | 3/2014 | Steiner et al. | |
| 2009/0098617 A1 | 4/2009 | Burke et al. | |

(Continued)

FOREIGN PATENT DOCUMENTS

| | | |
|---|---|---|
| EP | 2 226 387 A2 | 9/2010 |
| WO | 2004081185 A2 | 9/2004 |

(Continued)

*Primary Examiner* — Melvin C Mayes
*Assistant Examiner* — Douglas B Call
(74) *Attorney, Agent, or Firm* — O'Connor & Company; Ryan P. O'Connor

(57) ABSTRACT

A method for fermenting carbohydrate-rich crops is provided. Sugar beet, sugar cane, sweet sorghum, tropical maize hybrids and fruits are rich in simple sugars; potato, sweet potato, cassava and yam are rich in starch; and Jerusalem artichoke is rich in inulin. This method uses vacuum infusion to infuse yeast into the intercellular space (apoplast) of the parenchyma tissue. The simple sugars diffuse into the apoplast, come into contact with the yeast and produce ethanol. Ethanol can be extracted from the crop by vacuum stripping or crushing or can be left inside the starchy crop to preserve it. In some variants, pectinase enzymes degrade the parenchyma cell walls to speed up diffusion of simple sugars to the yeast, speed up diffusion of amylase to starch granules or speed up diffusion of inulinase to insoluble inulin.

20 Claims, 1 Drawing Sheet

(56) References Cited

U.S. PATENT DOCUMENTS

| | | | | |
|---|---|---|---|---|
| 2010/0041119 | A1* | 2/2010 | Christensen | C08B 37/0057 435/162 |
| 2010/0196980 | A1* | 8/2010 | Smith | C12P 7/10 435/161 |
| 2011/0020891 | A1 | 1/2011 | Steiner et al. | |
| 2011/0053237 | A1* | 3/2011 | Soong | C12P 7/06 435/161 |
| 2011/0318803 | A1* | 12/2011 | Hitz | C12N 1/20 435/162 |
| 2012/0276593 | A1* | 11/2012 | Li | C12P 7/06 435/95 |
| 2013/0323822 | A1* | 12/2013 | Brevnova | C12N 15/52 435/254.21 |
| 2014/0290135 | A1* | 10/2014 | Carraro | C12N 15/8205 47/57.7 |
| 2014/0311889 | A1* | 10/2014 | Zaher | B01D 3/002 203/42 |
| 2015/0018584 | A1* | 1/2015 | Parekh | C13K 13/002 568/840 |

FOREIGN PATENT DOCUMENTS

| | | | |
|---|---|---|---|
| WO | WO 2009/046538 | * | 4/2009 |
| WO | 2009062751 A2 | | 5/2009 |
| WO | WO2012/084962 | * | 6/2012 |
| WO | WO 2013/155496 | * | 10/2013 |
| WO | 2015116742 A1 | | 8/2015 |

* cited by examiner

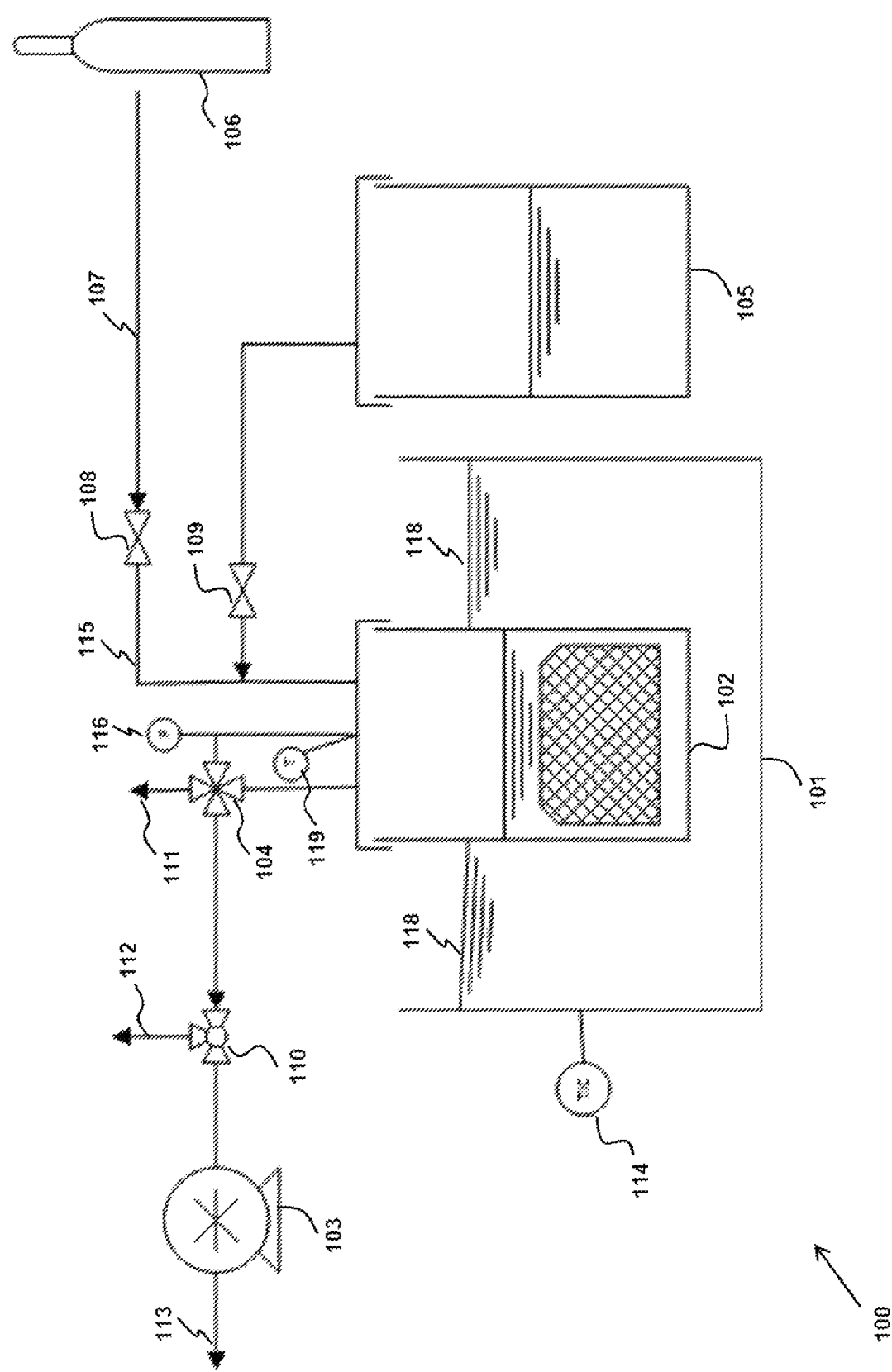

METHODS FOR FERMENTING CARBOHYDRATE-RICH CROPS

PRIORITY DATA

This patent application is a continuation application of U.S. patent application Ser. No. 14/940,390, filed Nov. 13, 2015, which claims priority to U.S. Provisional Patent App. No. 62/127,637, filed Mar. 3, 2015, and to U.S. Provisional Patent App. No. 62/139,881, filed Mar. 30, 2015, each of which is hereby incorporated by reference herein.

FIELD OF THE INVENTION

The present invention generally relates to methods for fermenting carbohydrate-rich crops.

BACKGROUND OF THE INVENTION

Many fermentation organisms convert carbohydrates to ethanol. The most widely used fermentation organisms, brewer's yeast and baker's yeast, are strains of *Saccharomyces cerevisiae*. Ethanol has significant economic value as beverages, transportation fuels and precursors for other organic compounds.

Fermentation organisms can directly convert glucose, fructose, maltose (glucose dimer) and sucrose (glucose-fructose dimer) to ethanol. Herein, monomers and dimers of glucose and fructose will be referred to as simple sugars and fermentation organisms that convert simple sugars to ethanol will be referred to as yeasts.

Yeasts ferment simple sugars to ethanol in an anaerobic (without oxygen) environment. One mole of glucose or fructose (or 0.5 mole of sucrose) is fermented to 2 moles of ethanol and 2 moles of carbon dioxide and gives off 118 kJ of heat. This means that fermenting an 18% sugar solution will result in a temperature rise of 34° C., which means that cooling of the fermentation medium is required. Fermenting 1 liter of an 18% sugar solution (1 mole of glucose) will also produce 2 moles of carbon dioxide, which has a volume of about 48 liters at 20° C. and atmospheric pressure. A typical yeast ferments most efficiently between 20-40° C. but has significant fermentation activity down to 5° C. (white wine is fermented between 7-15° C.). Yeast cells die gradually at temperatures above 42° C. *Saccharomyces cerevisiae* is relatively insensitive to pH and will ferment in a pH range from 2.9 to 7.2. This is described in more detail in Arroyo-López, "Effects of temperature, pH and sugar concentration on the growth parameters of *Saccharomyces cerevisiae*, S. kudriavzevii and their interspecific hybrid," *International journal of food microbiology* 131.2 (2009): 120-127, which is hereby incorporated by reference herein.

Most *Saccharomyces cerevisiae* strains have a diameter of approximately 10 microns. A *Saccharomyces cerevisiae* strain with a cell size of approximately 5 microns is Thermosacc® Dry, available from Lallemand Biofuels & Distilled Spirits, Duluth, Ga., USA. It produces ethanol concentrations up to 20% by volume (16% by weight), so carbohydrate-rich crops with up to 32% carbohydrates by weight can be fermented by this yeast. This means that a crop can be dehydrated before fermenting so that the resulting ethanol concentration is higher.

Yeast cells adhere to surfaces (such as parenchyma cells) in the presence of simple sugars. This is described Verstrepen and Klis, "Flocculation, adhesion and biofilm formation in yeasts," *Molecular microbiology* 60.1 (2006): 5-15, which is hereby incorporated by reference herein.

*Saccharomyces cerevisiae* is sold in freeze-dried form and is easy to handle. It is classified as GRAS (Generally Recognized as Safe) and is commonly consumed in the average diet—for example, bread is made with *Saccharomyces cerevisiae* yeast.

Starch is a polymer of glucose and inulin is a polymer of mostly fructose with glucose at one end. Before starch and inulin can be converted by yeast to ethanol, they must first be converted to simple sugars by amylases and inulinases, respectively, or by acids. Starch is insoluble in water in the temperature range for which yeast is active, and only about 5% of inulin is soluble in this same temperature range.

There are amylases available that convert starch to glucose efficiently in the temperature range that yeast operates efficiently. One example is the STARGEN® 002 enzyme formulation from DuPont Industrial Biosciences, USA. This contains an *Aspergillus kawachi* alpha-amylase expressed in *Trichoderma reesei* and a gluco-amylase from *Trichoderma reesei* that work synergistically to hydrolyze granular starch substrate to glucose. The endo-activity, alpha-amylase and exo-activity, gluco-amylase catalyze the complete hydrolysis of granular starch under a variety of ethanol fermentation conditions.

There are inulinases available that convert inulin to fructose efficiently in the temperature range that yeast operates efficiently. One example is the Fructozyme L enzyme formulation available from Novozymes A/S, Denmark.

Many crops contain carbohydrates within storage parenchyma cells. These carbohydrate-rich parenchyma cells generally have 10% to 20% carbohydrates in a single large vacuole with 80% to 90% water. These carbohydrates generally comprise simple sugars and polysaccharides. Herein, the parts of these carbohydrate-rich crops that contain a significant mass of carbohydrate-rich parenchyma cells will be referred to as carbohydrate-rich parenchyma tissue. All crops with carbohydrate-rich parenchyma tissue contain some amount of simple sugars in the parenchyma cells and some contain a significant amount of polysaccharides.

There are two types of crops with carbohydrate-rich parenchyma tissue, monocotyledons (monocots) in the grass family (Poaceae and Dioscorea) and dicotyledons (dicots). They differ in the way the parenchyma cells adhere to each other. Monocots adhere through both pectin and hemicellulose in the middle lamella and dicots adhere through pectin in the middle lamella.

The most widely cultivated crops with carbohydrate-rich parenchyma tissue in the stalks are sugar cane (*Saccharum officinarum*), sweet sorghum (*Sorghum bicolor*) and tropical maize hybrid (*Zea mays*). These are all monocots in the grass family (Poaceae). Sugar cane and tropical maize hybrid contain simple sugars in the storage parenchyma cells and sweet sorghum contains 90% simple sugars and 10% starch in the storage parenchyma cells.

The most widely cultivated crops with carbohydrate-rich parenchyma tissue in tubers are potato (*Solanum tuberosum*), sweet potato (*Ipomoea batatas*), cassava (*Manihot esculenta*), yam (genus *Dioscorea*) and Jerusalem artichoke (*Helianthus tuberosus*). Potato, sweet potato, cassava and Jerusalem artichoke are dicots while yam is a monocot. Potato, sweet potato, cassava and yam contain starch in the storage parenchyma cells and Jerusalem artichoke contains inulin in the storage parenchyma cells.

The most widely cultivated crops with carbohydrate-rich parenchyma tissue in fruits are apples, grapes and oranges. These are all dicots and contain glucose and fructose in the storage parenchyma cells.

There are well-known techniques for fermenting crops with carbohydrate-rich parenchyma tissue. Stalks are generally crushed between a series of rollers to extract the juice by bursting the parenchyma cells, and then the juice is separated from residual solids and fermented. Sugar beets are generally cut into small slices approximately 4 mm thick (cossettes) and the sugar is extracted with flowing hot water and is then fermented. Fruits are generally squeezed to extract sugar-rich juice which is then fermented. Starchy crops are generally converted to ethanol by heating the tuber above the gelatinization temperature and using amylases with the gelatinized starch, followed by fermentation of the glucose. Inulin-rich crops are generally fermented by heating until the inulin solubilizes, extracting the juice, using acid hydrolysis to convert to fructose and then fermenting the fructose. All of these techniques are quite capital-intensive.

The storage parenchyma cells in carbohydrate-rich parenchyma tissue are thin-walled polyhedral cells. Sugar beet parenchyma cells have a diameter of approximately 100 microns with a wall thickness of about 2 microns. The parenchyma cells in stalks are approximately 360 microns long and 60 microns in diameter with a wall thickness of about 2 microns. The characteristics of storage parenchyma tissue are described in more detail in Gibson, "The hierarchical structure and mechanics of plant materials," *Journal of The Royal Society Interface* 9.76 (2012): 2749-2766, which is hereby incorporated by reference herein.

The parenchyma cells are packed tightly together, but there are small gaps between them because the packing is imperfect. These gaps are known as the apoplast, or intercellular space. These gaps are interconnected, and water can flow through the parenchyma tissue through these gaps. There is more detail about water flow through the apoplast in Steudle, "Water transport in plants: role of the apoplast," *Plant and Soil* 187.1 (1996): 67-79, which is hereby incorporated by reference herein.

Water flows through the apoplast in sugar beet parenchyma tissue in the axial direction (up/down) but is limited in the radial direction (in/out) by the casparian strips in the roots. This is described in more detail in Amodeo, "Radial and axial water transport in the sugar beet storage root," *Journal of Experimental Botany* 50.333 (1999): 509-516, which is hereby incorporated by reference herein.

Similarly, water flows through the apoplast in parenchyma tissue of carbohydrate-rich stalks in the axial direction, but is limited by the internode length (the continuous sections of the stalk). Water doesn't flow in the radial direction because the outer part of the stalk is impenetrable to water. The internode of most carbohydrate-rich stalks is between 100 mm and 300 mm in length.

The apoplast (intercellular space) of sugar cane is sufficiently large to be colonized by a variety of bacteria. This is described in more detail in Dong, "A nitrogen-fixing endophyte of sugarcane stems (a new role for the apoplast)," *Plant Physiology* 105.4 (1994): 1139-1147 and in Tejera, "Nitrogen compounds in the apoplastic sap of sugarcane stem: Some implications in the association with endophytes," *Journal of plant physiology* 163.1 (2006): 80-85, both of which are hereby incorporated by reference herein. Similarly, the apoplast of other species of carbohydrate-rich parenchyma tissue is large enough to be colonized by bacteria.

It is possible to fill the apoplast of carbohydrate-rich parenchyma tissue by using vacuum infusion (also called vacuum impregnation). This involves surrounding the parenchyma tissue with a liquid, applying a vacuum, waiting for liquid and gas to be expelled from the parenchyma tissue, releasing the vacuum and waiting for the liquid to fill the apoplast. This is described in more detail in Gras, "The response of some vegetables to vacuum impregnation," *Innovative Food Science & Emerging Technologies* 3.3 (2002): 263-269, which is hereby incorporated by reference herein.

Carbohydrate-rich parenchyma tissue often contains up to 20% (by mass) carbohydrates. The parenchyma cell wall provides strength to the parenchyma cell and the cell membrane keeps the contents of the cell from leaking out of the cell. The cell wall is permeable to sucrose and other simple sugars. The cell membrane can be denatured by heat, generally above 70° C., which increases the diffusion coefficient of simple sugars through the cell membrane. This is the technique normally used to extract sucrose from sugar beets—the cell membrane is denatured by heat and then the sucrose diffuses out of the sugar beet into hot water. The diffusion coefficient of sucrose through denatured sugar beet tissue is about five times higher than through non-denatured sugar beet tissue, which is described in more detail in Bessadok-Jemai et al., "Modeling the kinetic of solute diffusion from sugarbeet particles based on electric conductivity measurements," *International Journal of Physical Sciences* 6.28 (2011): 6464-6468, which is hereby incorporated by reference herein.

Parenchyma cells can be macerated (separated from each) by either heat or enzymes. When the parenchyma cells are macerated, the cell membrane is also breached, both from mechanical action and from enzymes that are released from the cell wall. This causes the contents of the vacuoles to leak out of the parenchyma cells and causes enzymes to more easily diffuse into the vacuoles. This also provides a retting action, where the water in the parenchyma cells can be more easily removed by squeezing or evaporation. Any combination of pectin lyase, pectate lyase and polygalacturanase macerate parenchyma cells in dicots, while pectin lyase and xylanase macerate parenchyma cells in monocots. This is described in Ishii, "Enzymes for the isolation of protoplasts," *Plant Protoplasts and Genetic Engineering* I. Springer Berlin Heidelberg, 1989, 23-33, which is hereby incorporated by reference herein.

Pectate lyase and polygalacturanase, when they degrade pectin, also produce methanol which is often an undesirable product when producing ethanol. Pectin lyase degrades pectin without producing methanol as a byproduct and xylanase doesn't produce any alcohols. There are pectin lyases available that operate in the same pH and temperature range as yeast, in particular pectin lyase from *Aspergillus niger*, with an optimum pH of 5.5 and an optimum temperature of 35° C. This is described in Yadav et al., "Pectin lyase: a review," *Process Biochemistry* 44.1 (2009): 1-10, which is hereby incorporated by reference herein. One example of a pectin lyase that operates in the same pH and temperature range of yeast is the "Pectinei® Ultra Color" enzyme formulation available from Novozymes A/S, Denmark.

When fermenting, yeast produces large amounts of carbon dioxide ($CO_2$). Carbonic acid is formed by the dissolution of $CO_2$ in water. When fermenting, the partial pressure of $CO_2$ is 100 kPa (1 atm) and the pH of this solution is about 3.92. Yeast ferments well at this pH, pectin lyase enzymes from *Aspergillus niger* (such as Pectinex Ultra Color) have significant activity at this pH, granular starch hydrolyzing enzymes (such as STARGEN) have significant activity at this pH, and inulinase enzymes (such as Fructozyme L) have significant activity at this pH. Similarly, all of these enzymes have significant activity in the temperature range of yeast (25° C. to 40° C.).

The harvest temperature of sugar beet can be quite cold, often below 10° C. and the harvest temperature of sugar cane, sweet sorghum and tropical maize hybrids can be below 20° C. However, the heat released by fermentation of simple sugars in the apoplast of carbohydrate-rich parenchyma tissue will rapidly increase the temperature of this tissue to the temperature range where enzymes have significant activity.

The rate of fermentation is heavily influenced by the concentration of yeast cells. Sugar cane fermentation in typical mills in Brazil can take between 6 to 10 hours, but this requires high concentrations (10% w/w) of yeast and yeast cell recycling. This is described in more detail in Basso, "Ethanol production in Brazil: the industrial process and its impact on yeast fermentation," *INTECH Open Access Publisher*, 2011, which is hereby incorporated by reference herein. Wine or beer fermentation, with lower concentrations of yeast, can take up to a week.

One significant problem with current techniques for fermenting sugars to ethanol is bacterial contamination, in particular contamination by *Lactobacillus*. Without wishing to be bound by any particular theory, it is believed that turbulent mixing propagates bacteria throughout the fermentation medium, and since the contaminating bacteria can out-compete yeast, there is significant contamination. Without mixing, and without a gradient in sugar concentration (caused by uniformly distributing yeast in the carbohydrate-rich parenchyma tissue), any possible bacterial contamination remains localized and is unable to outcompete yeast across the whole biomass volume. This is described in Kundiyana et al., "Influence of temperature, pH and yeast on in-field production of ethanol from unsterilized sweet sorghum juice," *biomass and bioenergy* 34.10 (2010): 1481-1486, which is hereby incorporated by reference herein.

Because the parenchyma cells are so small, it takes a lot of energy to crush them or to extract the sugar from them with hot water. Almost 35% of the capital and operating costs of producing sugar from stalks is due to the cost of crushing. Similarly, much of the cost of producing sugar from sugar beets is due to the cost of hot water extraction. The economics of crushing sugar cane is described in more detail in Gbaboa, "Comparative study on cane cutter/juice expeller and roller model Sugarcane juice extraction systems," *INT J CURR SCI* 2013, 7: E 55-60, which is hereby incorporated by reference herein. It would reduce the costs of extracting sugars if the need for crushing or hot water extraction could be eliminated.

The bulk density of sugar beets is about 769 kg/m$^3$ and the bulk density of billets (cut sections) of sugar cane, sweet sorghum and tropical maize hybrids (i.e. stalks) is about 350 kg/m$^3$. If the sugar content is about 18%, this results in a sugar density of 138 kg sugar per cubic meter of sugar beets and 63 kg sugar per cubic meter of sugar cane, sweet sorghum and tropical maize hybrids. Since transportation costs are primarily a function of volume (and not weight), and since crops are often harvested significant distances from where they're processed, it is quite expensive to transport sugars at such low densities since only 5% to 10% of the volume of a truck is taken up by sugar. It is desired to reduce the cost of making ethanol from carbohydrate-rich crops by making ethanol at (or close to) the harvest site of these crops, reducing transportation costs.

Parenchyma cells in carbohydrate-rich parenchyma tissue are living tissue and therefore respire (breathe) after harvest. Respiration involves converting oxygen and sugar in the parenchyma cells to carbon dioxide and energy to maintain the cell. After sugar beets are harvested, about 200 g of sugar per day per metric ton of sugar beet are consumed by respiration, and in the first 5 days after harvest about 600 to 1500 g of sugar per day per metric ton of sugar beet are consumed by respiration. If sugar beets are about 18% sugar by weight, there is about 180 kg sugar in a metric ton of sugar beet, resulting in a loss of between 0.3% to 0.8% of sugar per day in the first 5 days and 0.1% of sugar per day in subsequent days. Given that sugar beets can be stored for 100 days before being processed, they can lose up 10% of their sugar content due to respiration. Sugar cane, sweet sorghum and tropical maize lose similar amounts of sugar when being stored. There is a need in the art to reduce the sugar lost to respiration by more rapidly converting carbohydrates to ethanol than current methods. Once the carbohydrates in crops are converted to ethanol, they can be stored for long periods, allowing continuous removal of the ethanol year round. It is desired to more efficiently use the capital invested in roller extraction, ethanol stripping and distillation by using this equipment year round, not just during the harvest season.

If sugar beets are stored in anaerobic (without oxygen) conditions, microorganisms will colonize the beets and after 21 days will completely ferment all sugar in the beets, mostly to lactic acid and acetic acid. Since the outer layer of the sugar beets are often abraded and damaged by harvesting, microorganisms can more easily penetrate the outer layers of the sugar beet, leading to sugar losses due to fermentation to lactic acid and acetic acid. Similarly, sugar cane, sweet sorghum and tropical maize hybrid are more susceptible to microorganisms penetrating the pith because the cane has been cut open into billets during harvesting.

Much of the capital cost and operating cost of producing ethanol from carbohydrate-rich crops is the cost of heating the feedstock. These costs could be reduced (or eliminated) by using the self-heating from energy released by fermentation.

Some techniques for producing ethanol from carbohydrate-rich crops require pretreatment or fermentation inside a pressure vessel. Because pressure vessels have a danger of exploding and require more strength than an unpressurized vessel, it would be beneficial to not require a pressure vessel.

Another significant capital cost and operating cost of producing ethanol from carbohydrate-rich crops is the cost of cooling the fermentation reactor. It would be desirable to use low-cost passive cooling such as blowing air over metal walled tanks or circulating cool carbon dioxide gas through the crop.

SUMMARY OF THE INVENTION

The invention provides a process for producing fermentation products from carbohydrate-rich plant parenchyma tissue, the process comprising the steps of:

(a) providing the carbohydrate-rich plant parenchyma tissue at a crop temperature;

(b) combining the carbohydrate-rich plant parenchyma tissue with an aqueous reagent solution at a reagent temperature containing a fermentation organism;

(c) exposing the carbohydrate-rich plant parenchyma tissue to a gas-phase preparation pressure for a preparation time, either prior to step (b) or following step (b), wherein the gas-phase preparation pressure is less than atmospheric pressure;

(d) exposing the carbohydrate-rich plant parenchyma tissue to a gas-phase infusion pressure for an infusion time, wherein the gas-phase infusion pressure is greater than the gas-phase preparation pressure; and (e) maintaining a gas-phase fermentation pressure for a fermentation time to produce fermentation products within the carbohydrate-rich plant parenchyma tissue, wherein the gas-phase fermentation pressure is greater than the gas-phase preparation pressure and wherein at least 25% of the mass of the fermentation products is ethanol.

In preferred embodiments, the carbohydrate-rich plant parenchyma tissue is selected from the group consisting of sugar cane stalks, sweet sorghum stalks, tropical maize hybrid stalks, sugar beet tubers, apples, grapes and oranges. In some embodiments, the carbohydrate-rich plant parenchyma tissue is selected from the group consisting of potato tubers, sweet potato tubers, cassava tubers, yam tubers and Jerusalem artichoke tubers.

In some embodiments, the aqueous reagent solution contains pectinase enzymes. In some embodiments, the aqueous reagent solution contains xylanase enzymes. In some embodiments, the aqueous reagent solution contains amylase enzymes. In some embodiments, the aqueous reagent solution contains inulinase enzymes.

In preferred embodiments, the crop temperature is from about 5° C. to about 40° C.

In preferred embodiments, the gas-phase preparation pressure is from about 105% to about 200% of the water equilibrium pressure at the greater of the crop temperature and the reagent temperature.

In preferred embodiments, the preparation time is from about 1 minute to about 1 hour.

In preferred embodiments, the fermentation organism is *Saccharomyces cerevisiae*.

In preferred embodiments, the reagent temperature is from about 20° C. to about 40° C.

In preferred embodiments, the aqueous reagent solution is homogenized. In some embodiments, the process further comprises mixing the aqueous reagent solution using turbulent energy in the range of about 0.15 W/kg to about 50 W/kg.

In preferred embodiments, the infusion time is from about 1 minute to about 1 hour.

In preferred embodiments, the fermentation time is from about 6 hours to about 7 days.

In preferred embodiments, the fermentation pressure is atmospheric pressure.

In some embodiments, the process further comprises maintaining the carbohydrate-rich plant parenchyma tissue in an anaerobic environment for a crop preservation time subsequent to the completion of the fermentation time.

In preferred embodiments, the process further comprises recovering the fermentation products by vacuum stripping. In some embodiments, the process further comprises recovering the fermentation products by crushing. In some embodiments, the process further comprises draining the aqueous reagent solution, either prior to step (e) or following step (e).

BRIEF DESCRIPTION OF THE DRAWING

FIG. 1 is a schematic drawing of an experimental apparatus used in embodiments and examples of the present invention.

DETAILED DESCRIPTION OF EMBODIMENTS OF THE INVENTION

The methods, processes, and systems of the present invention will be described in detail by reference to various non-limiting embodiments and figure(s).

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing parameters, conditions, results, and so forth used in the specification and claims are to be understood as being modified in all instances by the term "about." Accordingly, unless indicated to the contrary, the numbers set forth in the following specification and attached claims are approximations that may vary depending upon specific algorithms and calculations.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

No embodiments described herein shall be limited by any theory or speculation regarding reaction mechanisms, mass-transfer mechanisms, or descriptions of feedstocks or products.

The present invention is premised on a technical solution to the problem that producing fermentation products from carbohydrate-rich plant parenchyma tissue is expensive because of the large amount of energy and capital required for efficiently crushing or extracting with diffusion into hot water. This invention uses an alternative approach of infusing fermentation reagents under vacuum into the apoplast of carbohydrate-rich plant parenchyma tissue, allowing to ferment and then separating the resulting ethanol solution using low-cost techniques such as vacuum stripping. Principles of the invention are demonstrated in the Examples herein.

The present invention is also premised on a technical solution to the problem of degradation of starch-rich and inulin-rich crops after harvesting and before processing or consumption. This invention uses an approach of infusing fermentation organisms under vacuum into the apoplast of parenchyma tissue to ferment the simple sugars to ethanol, thus depriving other organisms of simple sugars needed to colonize and consume the starch or inulin. This results in a typical loss of 0.1% of the mass of the carbohydrate-rich tissue and the benefit of protecting the starch or inulin against degradation. Once the simple sugars are fermented, the only organisms that can degrade these parenchyma tissues are fungi that grow on pectin, organisms that grow on ethanol and organisms that grow on starch or inulin.

Most fungi that grow on pectin are aerobic, so keeping the environment anaerobic prevents these fungi from colonizing the parenchyma tissue. The anaerobic fungi that grow on pectin, especially *Rhizopus oryzae*, also require glucose to grow on pectin, so keeping the environment free of glucose as well as anaerobic prevents these fungi from colonizing the parenchyma tissue.

Organisms that grow on ethanol, especially *Acetobacter*, are also aerobic, so keeping the environment anaerobic prevents these organisms from converting ethanol to acetic acid.

Organisms that grow on starch, especially *Bacillus subtilis*, need to get access to the starch granules inside the parenchyma tissue. Without wishing to be bound by any particular theory, it is believed that the removal of glucose in the apoplast and inside the parenchyma cells causes organisms like *Bacillus subtilis* do not have sufficient energy to be motile within the parenchyma tissue.

Yeast produces large amounts of carbon dioxide while fermenting, and infusing yeast into carbohydrate-rich plant parenchyma tissue forms a foam on the outside of this tissue during fermentation and expels liquid from this tissue by the action of bubble formation inside the tissue. Surprisingly, yeast do not get expelled by these bubbles, and the yeast can continue fermentation until all simple sugars are fermented.

Without wishing to be bound by any particular theory, it is believed that the adhesion of yeast cells to parenchyma cells in the presence of glucose is stronger than the forces of the carbon dioxide bubbles acting to expel the yeast from the parenchyma tissue.

This invention is also premised on the fact that the diffusion rate of simple sugars through the cell membrane in parenchyma cells of carbohydrate-rich crops is sufficient to enable fermentation organisms in the apoplast to ferment the simple sugars within the parenchyma cells at a high rate. The ethanol then diffuses into the parenchyma cells. In some variations, the parenchyma cell walls are not degraded, maintaining the structural strength of the crop which enables use of low-cost vacuum stripping. In other variations, pectinases degrade the parenchyma cell walls, increasing the speed of fermentation and reducing the energy needed for dewatering the tissue after removal of the ethanol.

In some variations, the invention provides a process for producing fermentation products from carbohydrate-rich plant parenchyma tissue, the process comprising the steps of:

(a) providing carbohydrate-rich plant parenchyma tissue at a crop temperature;

(b) combining the carbohydrate-rich plant parenchyma tissue with an aqueous reagent solution at a reagent temperature containing a fermentation organism;

(c) exposing the carbohydrate-rich plant parenchyma tissue to a gas-phase preparation pressure for a preparation time, either prior to step (b) or following step (b), wherein the gas-phase preparation pressure is less than atmospheric pressure;

(d) exposing the carbohydrate-rich plant parenchyma tissue to a gas-phase infusion pressure for an infusion time, wherein the gas-phase infusion pressure is greater than the gas-phase preparation pressure; and (e) maintaining a gas-phase fermentation pressure for a fermentation time to produce fermentation products within the carbohydrate-rich plant parenchyma tissue, wherein the gas-phase fermentation pressure is greater than the gas-phase preparation pressure and wherein at least 25% of the mass of the fermentation products is ethanol.

Those skilled in the art will recognize that the gas-phase preparation pressure can be applied either before or after combining the carbohydrate-rich plant parenchyma tissue with an aqueous reagent solution. Gras describes combining before applying a vacuum, and the examples below describe combining after applying a vacuum. Combining before applying a vacuum, as described by Gras, has the advantage of a faster pump-down time, since less volume needs to be evacuated. However, it has the disadvantage of having a higher hydrostatic pressure at the bottom of a larger vessel. For a vessel only 1 m deep, this disadvantage isn't significant, but for deeper vessels, this disadvantage may be significant.

Those skilled in the art will recognize that there are a wide range of fermentation organisms that produce ethanol, and these fermentation organisms adhere to surfaces in the presence of glucose.

Vacuum infusion can be done with a vessel of modest strength filled to the top with tubers or stalks and with a rubber bladder on the top—when a vacuum is applied, the strength of the crop itself is what supports the atmospheric pressure of 100 kPa on the outside of the vessel. This results in a very low cost vacuum infusion vessel, and the energy cost of pumping the air out of this vacuum infusion vessel is also quite low. In some embodiments, this vacuum infusion vessel can be the truck that brings in the crop from the field, with a rubber bladder inserted over the top, for example.

Once the aqueous reagent solution is infused, the crop can be transferred to an even lower-cost fermentation vessel. This lower-cost fermentation vessel doesn't need to be air-tight, just tight enough to hold in the carbon dioxide that is produced by the fermentation to keep the fermentation anaerobic, thus preventing the degradation of the ethanol by *Acetobacter* bacteria.

In preferred embodiments, the carbohydrate-rich plant parenchyma tissue is selected from the group consisting of sugar cane stalks, sweet sorghum stalks, tropical maize hybrid stalks, sugar beet tubers, apples, grapes and oranges. These all primarily contain simple sugars in the parenchyma tissue and can be fermented with yeast, without requiring infusion of pectinase. Optionally, pectinase speeds up the fermentation, albeit at the cost of complexity and the additional cost of the enzymes.

In some embodiments, the carbohydrate-rich plant parenchyma tissue is selected from the group consisting of potato tubers, sweet potato tubers, cassava tubers, yam tubers and Jerusalem artichoke tubers. These crops contain a small amount of simple sugars, between 0.01% to 2% by weight, and the remainder of the carbohydrates as polysaccharides. For preserving these crops, infusion of yeast will convert the small amounts of simple sugars to ethanol. For converting the polysaccharides in these crops to ethanol, an additional infusion of a pectinase and an amylase or inulinase is required.

In some embodiments, the aqueous reagent solution contains pectinase enzymes. In some embodiments, the aqueous reagent solution contains xylanase enzymes. In some embodiments, the aqueous reagent solution contains amylase enzymes. In some embodiments, the aqueous reagent solution contains inulinase enzymes. The preferred pectinase enzyme is pectin lyase in embodiments that require minimal production of methanol as a byproduct. A combination of pectinase and xylanase are needed to break down the parenchyma cell walls in dicots.

In preferred embodiments, the crop temperature is from about 5° C. to about 40° C. This temperature range is needed because the fermentation organisms are active in this range.

In preferred embodiments, the gas-phase preparation pressure is from about 105% to about 200% of the water equilibrium pressure at the greater of the crop temperature and the reagent temperature. The pressure needs to be as low as possible while still preventing the crop or the reagent from boiling.

In preferred embodiments, the preparation time is from about 1 minute to about 1 hour. Some crops take longer than others to evacuate the gas from the apoplast, in particular sugar cane and sweet sorghum.

In preferred embodiments, the fermentation organism is *Saccharomyces cerevisiae*. This organism has the highest ethanol tolerance of any fermentation organism and many hybrids are available.

In preferred embodiments, the reagent temperature is from about 20° C. to about 40° C. Fermentation organisms thrive in this temperature range.

The reagent temperature should be low enough so the water in the aqueous reagent solution does not boil at the preparation pressure, where boiling entails the fast release of vapor as large bubbles. Since water is normally the main constituent of the aqueous reagent solution, water equilibrium data can be used to determine the reagent temperature at a given preparation pressure and vice versa. For instance, if the reagent temperature is about 38° C., the preparation pressure should be more than about 7 kPa.

In preferred embodiments, the aqueous reagent solution is homogenized. In some embodiments, the process further comprises mixing the aqueous reagent solution using turbulent energy in the range of about 0.15 W/kg to about 50 W/kg.

Sufficient turbulent energy is used so that the Kolmogorov length scale is on the order of less than the apoplast free length (e.g., about 10 microns). Using the Kolmogorov length scale, and knowing the kinematic viscosity of water at 20° C. is about $10^{-6}$ m$^2$/s, the energy required to mix the reagents and process water to a 10-micron scale is about 50 W/kg. Similarly, mixing to a 20-micron scale requires about 5 W/kg, and mixing to a 50 micron scale requires about 0.15 W/kg.

A person of ordinary skill in the art will recognize that there are many simple mixing devices than can mix with this kind of energy. One such simple mixing device is a 25-mm diameter plastic pipe 8 meters long with a pipe roughness of 0.0014, infusing from atmospheric pressure (100 kPa) to a vacuum of 20 kPa with a 2.8 liter/sec (6 CFM) vacuum pump maintaining the vacuum during infusion. The power dissipated in the pipe due to pressure drop is 226.4 W. The total amount of liquid in the pipe is 4.05 kg, so the power dissipated per kg is about 56 W/kg, which is adequate to mix at a 10-micron scale (the exemplary flow rate is sufficient to infuse 18 m$^3$ in 1.8 hours).

In preferred embodiments, the infusion time is from about 1 minute to about 1 hour. Experiments have shown that the efficiency of conversion of sugars is relatively insensitive to infusion time.

In preferred embodiments, the fermentation time is from about 6 hours to about 7 days. Experiments have shown that the fermentation time with a concentration of yeast of about 2 cells per parenchyma cell results in the fermentation time of about 6 hours to 20 hours, depending on the type of carbohydrate-rich plant parenchyma.

In preferred embodiments, the fermentation pressure is atmospheric pressure. Since $CO_2$ is continually produced, and since pressure vessels are expensive and dangerous, venting $CO_2$ at atmospheric pressure is less expensive.

In some embodiments, the process further comprising maintaining the carbohydrate-rich plant parenchyma tissue in an anaerobic environment for a crop preservation time subsequent to the completion of the fermentation time. When the environment is anaerobic and there are no simple sugars in the apoplast or parenchyma cells, fungi and bacteria can't grow on the pectin or ethanol.

In preferred embodiments, the process further comprises recovering the fermentation products by vacuum stripping. In some embodiments, the process further comprises recovering the fermentation products by crushing. In some embodiments, the process further comprises draining the aqueous reagent solution, either prior to step (e) or following step (e).

Vacuum stripping is preferred because it is an efficient and cost-effective technique for recovering fermentation products. Vacuum stripping of ethanol can be done with a similar vessel as vacuum infusion, but with the added capability to heat the crop. Draining the aqueous reagent solution results in a higher percentage of ethanol in the stripped vapor.

A person of ordinary skill in the art will recognize that the temperature rise during fermentation can be limited to about 38° C. with a variety of low-cost techniques, especially if the fermentation takes place over roughly 20 hours.

A person of ordinary skill in the art will recognize that known apparatus may be employed for the processes, systems, and methods disclosed herein. The processes herein may be batch, continuous, semi-continuous, or pseudo-continuous. Any reference to "vessel" or "reactor" herein shall be construed to mean one or a plurality of such apparatus (such as in series or in parallel). Various flow patterns may be desired or observed. With chemical reactions and simultaneous mass-transfer processes involving multiple phases, the fluid dynamics can be quite complex. Depending on the specific design, flow patterns may approach plug flow or well-mixed flow.

The throughput, or process capacity, may vary widely from small laboratory-scale units to full commercial-scale biorefineries, including any pilot, demonstration, or semi-commercial scale. In various embodiments, the process capacity is at least about 1 kg/day, 10 kg/day, 100 kg/day, 1 ton/day (all tons are metric tons), 10 tons/day, 100 tons/day, 500 tons/day, 1000 tons/day, 2000 tons/day, or higher.

The overall system may be at a fixed location, or it may be made portable. The system may be constructed using modules which may be simply duplicated for practical scale-up.

Various probes may allow precise process monitoring and control across various stages of the process, up to and potentially including all stages of the process. Precise process monitoring would be expected to result in yield and efficiency improvements, both dynamically as well as over a period of time when operational history can be utilized to adjust process conditions (including pressure cycling programs). In some embodiments, a reaction probe is disposed in operable communication with a process zone. Such a reaction probe may be useful to extract liquid samples and analyze them, in order to determine extent of hydrolysis, or sugar profile, etc. Process adjustments may be based on measurements, if deemed necessary or desirable, using well-known principles of process control (feedback, feedforward, proportional-integral-derivative logic, etc.).

Solid, liquid, and gas streams produced or existing within the process can be independently recycled, passed to subsequent steps, or removed/purged from the process at any point.

EXAMPLES

The following examples demonstrate principles of this invention. The vacuum infusion of yeast and enzymes described above has been shown, by experimental evidence, to be useful for fermenting carbohydrate-rich crops.

The experimental apparatus of FIG. 1 is designed to reproduce industrial process functionality as far as temperature, pressure, and flow control of an industrial unit. It differs from an industrial unit in the loading and unloading of the crop (the sample). The experimental apparatus is used in all examples below.

With reference to FIG. 1, the experimental apparatus 100 consists of a main infusion vessel 102, which under operation is kept almost completely immersed inside a thermostatic bath 101 which can operate over a wide range of temperature and whose precise temperature control is ensured by a temperature controller 114. The infusion vessel 102 is closed with a removable and sealed lid 118. The infusion vessel 102 and the sealed lid 118 are designed to be able to hold and sustain vacuum conditions as required by the process conditions. The desired amount of sample material 117 can be placed inside the infusion vessel 102. The infusion vessel 102 can be supplied with $CO_2$ via a $CO_2$ cylinder 106 and a $CO_2$ line 107. On the $CO_2$ line 107, a flow/pressure regulator 108 is used to set the pressure at which the $CO_2$ is delivered to the infusion vessel 102. A vacuum pump 103 is used to evacuate and maintain vacuum inside the infusion vessel 102. A pressure indicator 116 and temperature indicator 119 are installed on the infusion vessel 102. The infusion vessel 102 is connected through a gate valve 109 to a container 105 with prepared aqueous reagent solution. The vacuum pump 103 is connected to the infusion vessel 102 via a line where a pressure regulator 110 is installed. The pressure regulator 110 allows the infusion vessel 102 pressure to be regulated over a wide range of vacuum levels, while the vacuum pump 103 is operated at constant speed. A vent 112 on the pressure regulator 110 is connected to a gas counter. A four-way valve 104 on the gas outlet of the infusion vessel 102 allows one to remove samples from the sample port 111, insulate the infusion vessel 102, cycle the pressure 116, and recycle part of the sample back into the infusion vessel 102 without altering the pressure and the gas cap composition inside it.

The experimental procedure for the Examples below is as follows. Premixed aqueous reagent solution is prepared separately according to the specific needs of the experiment; optionally the aqueous reagent solution may be preheated to a temperature of interest. The crop sample is placed inside the infusion vessel 102. No liquid is present in the infusion vessel 102. The infusion vessel 102 is placed in thermostatic bath 101, which is operating at the temperature set for the experiment. Once the lid 118 is placed on top of the infusion vessel 102, using the vacuum pump 103 and $CO_2$ from the line 107, any air is flushed and a $CO_2$ atmosphere is formed on top of the sample. Once the flushing of any residual air is ensured, the flow of fresh $CO_2$ from the line 107 is interrupted by operating on the flow controller 115. The pressure in the infusion vessel 102 is allowed to drop to the level defined in the experiment by controlling it via the pressure regulator 110.

Once pressure and temperature are stabilized at the desired level, the free liquid that was expelled from the crop when the pressure dropped is optionally drained out from the vessel using the sample port 111 and saved for further analysis. Then the gate valve 109 is opened and the premixed aqueous reagent solution is allowed to enter the infusion vessel 102 where the infusion takes place. The amount of sample material is set in such a way that, depending upon the bulk density of the material, the sample is completely submerged once the feeding of the liquid is interrupted. By accurately selected temperature and pressure, boiling of the liquid can be avoided (boiling causes large release of gas bubbles). After the infusion is completed and the gate valve 109 is closed, a partial pressure of 1.0 atm of $CO_2$ is established by opening and regulating the flow and pressure controller 108.

Once the liquid has infused into the crop at a pressure of 1.0 atm for the desired time, the free liquid is optionally drained out from the vessel using the sample port 111.

The experiment then can proceed for the duration desired. If a liquid sample is needed during the experiment, a syringe may be connected to the four-way valve 104 sample port 111 which is set as to allow the syringe to be filled with liquid. Any residual liquid flows back into the vessel through the four-way valve manifold once the syringe is removed and the sample port 111 is closed.

The progress of fermentation is measured by gas produced at vent 112 with a MilliGascounter, type MGC-1, from Dr.-Ing. Ritter Apparatebau GmbH & Co. KG in Bochum, Germany. The amount of gas produced is measured at the milliliter resolution over the period of the fermentation. The fermentation of 3.35 g of sugar (normally sucrose) generates 1 L of gas ($CO_2$), so the amount of sugar fermented, the rate of fermentation and the total amount of sugar fermented can be inferred by the graph of gas produced over time.

The following examples use sugar beet from northern Minnesota, sugar cane from Florida and sweet sorghum from Tennessee. Juice from each was squeezed out and sugar content in Brix was measured with a digital refractometer. Samples of each were bone dried to determine percent dry solids. These were combined to calculate the percent (w/w) of sugars in these crops.

Note that the Brix measurement of sweet sorghum juice was adjusted by multiplying by about 0.8 to get the percentage by weight of total sugars. This is because sweet sorghum juice has more glucose and fructose than sugar beet or sugar cane juice, and the index of refraction of glucose and fructose differs from that of sucrose. This is described in Liu et al., "Refining bioethanol from stalk juice of sweet sorghum by immobilized yeast fermentation," *Renewable Energy* 33.5 (2008): 1130-1135, which is hereby incorporated by reference herein.

The sugar beet was computed to have 18% sugar by weight, the sugar cane was 14% sugar by weight and the sweet sorghum was 10% sugar by weight.

Example 1

Infusion of Water into Sugar Beet Parenchyma Tissue

Slices of sugar beet were cut radially to three different thicknesses, 6 mm, 12 mm and 18 mm. These slices were then cut into 25 mm square slices and all of the 25 mm square slices for each of the three thicknesses were weighed and put into three of the apparatus described above (FIG. 1). The gas cap was air for this example.

In Phase 1, a vacuum of 13 kPa was applied for 30 minutes, free water was removed, pressure was restored to 100 kPa and each cube was weighed.

In Phase 2, a vacuum of 13 kPa was applied for 30 minutes, water was infused under vacuum until the cube was covered, pressure was restored to 100 kPa, water infused into the parenchyma tissue for 30 minutes, free water was removed and then each cube was weighed.

In Phase 3, a vacuum of 13 kPa was applied for 30 minutes, free water was removed, pressure was restored to 100 kPa and each cube was weighed.

The result of this test are shown in Table 1 below and this result shows that about 10% of the mass of the parenchyma tissue exuded from the tissue when a vacuum was applied for 30 minutes. It also shows that about 6% of the mass of the parenchyma tissue could be infused with water under vacuum and that about half of this exuded from the tissue when a vacuum was applied again. More significantly, this example shows that infusion was almost identical in 6 mm thick tissue and 18 mm tissue.

TABLE 1

Mass of sugar beet slices

| Thickness | Initial mass | Phase 1 mass | Phase 2 mass | Phase 3 mass |
|---|---|---|---|---|
| 6 mm | 5.985 g | 5.389 g | 5.695 g | 5.604 g |
| 12 mm | 8.987 g | 8.358 g | 8.761 g | 8.312 g |
| 18 mm | 14.782 g | 13.194 g | 14.32 g | 13.557 g |

Example 2

Fermentation of Sugar Cane

Chopped sugar cane was infused with a slightly acidic yeast solution enriched with nitrogen-rich nutrients (Fermax from the BSG Corporation). Two different solutions were tested in duplicate, one using Thermosacc yeast and one using Distillamax yeast. Both yeasts are commercially available from Lallemand Biofuels & Distilled Spirits and differ in the average size of the cell bodies. The Thermosacc yeast has an average cell diameter of 5 microns and the Distillamax has an average cell diameter of 10 microns. After infusion was completed the carbon dioxide production was monitored through gas counters to estimate the fermentation progress. The following procedure was used:

1. Start heating thermostatic bath to 38° C.
2. Weigh approximately 50 g of sugar cane, then chop up into approximately one inch pieces, weighing the total amount of cane again after chopping.
3. Prepare two yeast solutions, one with 5 g/L Distillamax yeast, 1 g/L Fermax nutrients and one with 5 g/L Thermosacc (C6) Yeast, 1 g/L Fermax nutrients, buffering both to a pH of 3.5 with phosphoric acid.
4. Place sugar cane in sealed beakers in the thermostatic bath, and apply vacuum for 30 min to ensure complete evacuation of gas from the biomass.
5. Infuse approximately 200 g of the solution to each beaker.
6. Slowly restore atmospheric pressure creating an inert gas cap on top of the beaker content.
7. Open the gas venting valve to let gas flow through the gas flow meters.
8. Let fermentation run to completion while logging gas flow.

Samples with Thermosacc yeast and Distillamax yeast were run in duplicate, and the results with the highest gas yield are presented in Table 2. Both fermentations took a bit less than 8 hours to complete.

In both cases, the infusion allows the fermentation to occur inside the body of the sugar cane with minimum pre-processing of the substrate besides a coarse size reduction. Surprisingly, the smaller yeast cells appear more effective ensuring a larger conversion of sugar as demonstrated by the larger gas production. This result is consistent with the smaller yeast being able to diffuse more deeply inside the sugar cane apoplast. In both cases, vacuum infusion allows active in-situ fermentation as shown in Table 2.

TABLE 2

Efficiency of sugar cane fermentation

| Sample | Sample weight (g) | Sugar content (g) | Theoretical $CO_2$ production (L) | Actual $CO_2$ production (L) | Yield |
|---|---|---|---|---|---|
| Thermosacc | 44.10 | 6.17 | 1.84 | 1.80 | 97.8% |
| Distillamax | 43.10 | 6.03 | 1.80 | 1.20 | 66.6% |

Example 3

Fermentation of Sugar Beet

Coarsely chopped sugar beet pieces were infused with a slightly acidic yeast solution made Distillamax yeast by Lallemand Biofuels & Distilled Spirits. Different infusion times were used for each sample. After infusion was completed, the carbon dioxide production was monitored by the gas counters to estimate the fermentation progress. The following procedure was used:

1. Ensure that the thermostatic bath is at 38° C.
2. Weigh approximately 100 g of sugar beets, then chop up into pieces of approximately one-inch cubes, weighing the total beet again after chopping.
3. Prepare yeast solution with 5 g/L Distillamax yeast, buffering to a pH of 3.5 with phosphoric acid.
4. In the solution for samples 2 and 4 add an enzyme with pectinase activity at a loading of about 5 g per kg of dry biomass.
5. Place sugar beet sample in sealed beakers in the thermostatic bath, and apply vacuum for 30 min.
6. Infuse enough solution to submerge all beet pieces.
7. Release pressure instantly for samples 1 and 2 and slowly (about 5 minutes) for samples 3 and 4.
8. Connect to gas counters.

9. Let fermentation run to completion.

The sample size and amount of gas produced by fermenting each of these 4 samples of sugar beet are presented in Table 3. All fermentations took between 13 and 15 hours to complete. Infusion time does not have a significant impact on the overall sugar conversion yield, since this yield is above about 90% for the fast infusion cases (samples 1 and 2). Slow infusion seems to be slightly detrimental. The addition of pectinase enzyme—which breaks down the cell wall—appears to improve the fermentation and further illustrates the vacuum infusion ability to deliver in situ enzymatic and microbiological activity without mechanical mixing and minimum preprocessing of the biomass.

TABLE 3

Efficiency of sugar beet fermentation

| Sample | Sample weight (g) | Sugar content (g) | Theoretical $CO_2$ production (L) | Actual $CO_2$ production (L) | Yield |
|---|---|---|---|---|---|
| 1 | 92.623 | 16.67 | 4.98 | 4.50 | 90.4% |
| 2 | 91.826 | 16.53 | 4.93 | 4.75 | 96.2% |
| 3 | 92.269 | 16.61 | 4.96 | 4.40 | 88.7% |
| 4 | 90.944 | 16.37 | 4.89 | 4.48 | 91.6% |

Example 4

Fermentation of Sweet Sorghum

The same procedure for fermenting sweet sorghum was used as in Example 2 above. Instead of varying the type of yeast, Thermosacc yeast was used for both samples. One sample drained the liquid from the stalks after infusion, and the other didn't drain the liquid.

The results of these fermentations are presented in Table 4. Both fermentations took a bit less than 20 hours to complete.

Surprisingly, the efficiency of fermenting with the liquid drained from the stalks is higher than the efficiency of leaving the liquid around the stalks. In both cases, however, vacuum infusion allows active in-situ fermentation.

TABLE 4

Efficiency of sweet sorghum fermentation

| Sample | Sample weight (g) | Sugar content (g) | Theoretical $CO_2$ production (L) | Actual $CO_2$ production (L) | Yield |
|---|---|---|---|---|---|
| Drained | 51.1 | 5.11 | 1.53 | 1.52 | 99.3% |
| Not Drained | 52.0 | 5.20 | 1.55 | 1.33 | 85.8% |

Example 5

Fermentation of Potato

Coarsely chopped potato pieces were infused with a slightly acidic yeast solution made of Thermosacc yeast by Lallemand Biofuels & Distilled Spirits. One sample was additionally infused with α-amylase enzymes from BSG Handcraft in Shakopee, Minn., USA. This α-amylase has maximum activity at 66° C. and about 20% activity at 38° C. After infusion completed, the carbon dioxide production was monitored by the gas counters to estimate the fermentation progress. The following procedure was used:

1. Ensure that the thermostatic bath is at 38° C.
2. Weigh approximately 70 g of potato, then chop up into pieces of approximately one-inch cubes, weighing the total potato after chopping.
3. Prepare yeast solution with 5 g/L Thermosacc yeast, buffering to a pH of 3.5 with phosphoric acid.
4. In the solution for sample 2, add an enzyme with α-amylase activity at a loading of 5 g per kg of dry matter.
5. Place potato sample in sealed beakers in the thermostatic bath, and apply vacuum for 30 min.
6. Infuse enough solution to submerge all potato pieces.
7. Release pressure instantly.
8. Connect to gas counters.
9. Let fermentation run for about 120 hours.

The sample size and amount of gas produced by fermenting each of these 2 samples of potato are presented in Table 5. Those skilled in the art will recognize that there are about 0.5% to 2% simple sugars (sucrose+glucose) in the parenchyma cells, and about 18% starch in the potato, of which about 80% of the starch can be broken down to glucose, maltose and maltotriose by α-amylase. The fermentation of both samples took 14.5 hours before measurable gas was produced.

Without wishing to be bound by any particular theory, it is believed that this long induction time was partly caused by the initial $CO_2$ production being absorbed in the water in the potato, and the gas production began when the water in the potato was saturated with $CO_2$. Those skilled in the art will recognize that the solubility of $CO_2$ in water at 38° C. is about 1.6 g/L, that 0.076 L of potato tissue contains about 0.608 L of water, and that about 0.042 L of $CO_2$ will dissolve in a 0.076 L potato before the first bubble will appear.

After 120 hours of fermentation, sample 1 produced 0.155 L of gas and sample 2 produced 1.27 L of gas. Sample 1 produced no measurable gas between 72 hours and 120 hours, showing that all the simple sugars in the apoplast and the parenchyma cells were fermented and that no additional simple sugars were released from the starch granules. This shows that infusing yeast will preserve starch-rich parenchyma tissue.

The significantly higher gas production in sample 2 shows that the α-amylase diffused into the parenchyma cells and hydrolyzed about 40% of the starch granules to sugars that the yeast could ferment. The gas production was continuous through the 120 hour fermentation, with a slow decline. This example demonstrates that this technique can ferment starch granules inside the parenchyma cells by simply infusing yeast and amylase, without infusing pectinase. It also shows that the parenchyma cell membrane is permeable to amylase enzymes.

TABLE 5

Efficiency of potato fermentation

| Sample | Sample weight (g) | Sucrose + Glucose + Maltose (g) | Theoretical $CO_2$ production (L) | Actual $CO_2$ production (L) | Yield |
|---|---|---|---|---|---|
| Yeast only | 76 | 0.76 | 0.227 | 0.155 + 0.042 | 87% |
| Yeast + amylase | 74 | 10.65 | 3.18 | 1.27 | 40% |

In this detailed description, reference has been made to multiple embodiments and to the accompanying drawings in which are shown by way of illustration specific exemplary embodiments of the invention. These embodiments are described to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and figures described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims. In the case of conflict in definitions between the present disclosure and a dictionary or other reference, the present disclosure will be controlling.

What is claimed is:

1. A process for producing fermentation products from carbohydrate-rich plant parenchyma tissue, said process comprising the steps of:
    (a) providing carbohydrate-rich plant parenchyma tissue containing an apoplast at a crop temperature;
    (b) combining said carbohydrate-rich plant parenchyma tissue with an aqueous reagent solution containing a yeast, at a reagent temperature;
    (c) exposing said carbohydrate-rich plant parenchyma tissue to a gas-phase preparation pressure for a preparation time, either prior to step (b) or following step (b), wherein said gas-phase preparation pressure is less than atmospheric pressure;
    (d) exposing said carbohydrate-rich plant parenchyma tissue to a gas-phase infusion pressure for an infusion time, wherein said yeast infuses into said apoplast, and wherein said gas-phase infusion pressure is greater than said gas-phase preparation pressure;
    (e) draining free liquid that has not been drawn into said apoplast; and
    (f) after step (e), maintaining a gas-phase fermentation pressure for a fermentation time to produce fermentation products within said apoplast without reintroducing said aqueous reagent solution back to said carbohydrate-rich plant parenchyma tissue, wherein said gas-phase fermentation pressure is greater than said gas-phase preparation pressure, wherein said fermentation products are produced by fermentation of carbohydrates selected from the group consisting of simple sugars, simple sugars hydrolyzed from starch, simple sugars hydrolyzed from inulin, and combinations thereof, wherein at least 25% of the mass of said fermentation products is ethanol, and wherein at least 25% of the mass of said fermentation products is carbon dioxide, and wherein said carbon dioxide does not expel said yeast from said apoplast during said fermentation.

2. The process of claim 1, wherein said carbohydrate-rich plant parenchyma tissue is selected from the group consisting of sugar cane stalks, sweet sorghum stalks, tropical maize hybrid stalks, sugar beet tubers, apples, grapes, oranges, and combinations thereof.

3. The process of claim 1, wherein said carbohydrate-rich plant parenchyma tissue is selected from the group consisting of potato tubers, sweet potato tubers, cassava tubers, yam tubers, Jerusalem artichoke tubers, and combinations thereof.

4. The process of claim 1, wherein said aqueous reagent solution contains pectinase enzymes.

5. The process of claim 1, wherein said aqueous reagent solution contains xylanase enzymes.

6. The process of claim 1, wherein said aqueous reagent solution contains amylase enzymes.

7. The process of claim 1, wherein said aqueous reagent solution contains inulinase enzymes.

8. The process of claim 1, wherein said crop temperature is from about 5° C. to about 40° C.

9. The process of claim 1, wherein said gas-phase preparation pressure is from about 105% to about 200% of the water equilibrium pressure at the greater of said crop temperature and said reagent temperature.

10. The process of claim 1, wherein said preparation time is from about 1 minute to about 1 hour.

11. The process of claim 1, wherein said yeast is *Saccharomyces cerevisiae*.

12. The process of claim 1, wherein said reagent temperature is from about 20° C. to about 40° C.

13. The process of claim 1, wherein said aqueous reagent solution is homogenized.

14. The process of claim 13, said process further comprising mixing said aqueous reagent solution using turbulent energy in the range of about 0.15 W/kg to about 50 W/kg.

15. The process of claim 1, wherein said infusion time is from about 1 minute to about 1 hour, and wherein said infusion pressure is atmospheric pressure.

16. The process of claim 1, wherein said fermentation time is from about 6 hours to about 7 days.

17. The process of claim 1, wherein said fermentation pressure is atmospheric pressure.

18. The process of claim 1, said process further comprising maintaining said carbohydrate-rich plant parenchyma tissue in an anaerobic environment for a crop preservation time subsequent to the completion of said fermentation time.

19. The process of claim 1, wherein said process further comprises recovering said fermentation products by vacuum stripping.

20. The process of claim 1, wherein said process further comprises recovering said fermentation products by crushing.

* * * * *